United States Patent [19]
Bergersen

[11] Patent Number: 5,876,199
[45] Date of Patent: Mar. 2, 1999

[54] APPLIANCE ADAPTED TO FIT MANY MOUTH AND TOOTH SIZES FOR ORTHODONTIC CORRECTION AND OTHER USES

[75] Inventor: Earl O Bergersen, Winnetka, Ill.

[73] Assignee: Ortho-Tain, Inc., Bayamon, Puerto Rico

[21] Appl. No.: 920,034

[22] Filed: Aug. 28, 1997

[51] Int. Cl.⁶ .................................................. A61C 7/00
[52] U.S. Cl. ........................................................... 433/6
[58] Field of Search ................................ 433/6; 128/848, 128/861

[56] References Cited

U.S. PATENT DOCUMENTS

| | | | |
|---|---|---|---|
| D. 323,215 | 1/1992 | Bergersen | D24/180 |
| 3,478,429 | 11/1969 | Shilliday | 433/6 |
| 3,724,075 | 4/1973 | Kesling | 433/6 |
| 3,848,335 | 11/1974 | Bergersen | 433/6 |
| 3,898,736 | 8/1975 | Bergersen | 433/6 |
| 3,939,598 | 2/1976 | Bergersen | 433/6 |
| 3,950,851 | 4/1976 | Bergersen | 433/6 |
| 4,073,061 | 2/1978 | Bergersen | 433/6 |
| 4,139,944 | 2/1979 | Bergersen | 433/6 |
| 4,784,605 | 11/1988 | Bergersen | 433/6 |
| 4,799,884 | 1/1989 | Bergersen | 433/6 |
| 4,830,612 | 5/1989 | Bergersen | 433/6 |
| 4,898,535 | 2/1990 | Bergersen | 433/6 |
| 4,919,612 | 4/1990 | Bergersen | 433/6 |
| 5,028,231 | 7/1991 | Hall | 433/6 |
| 5,037,294 | 8/1991 | Bergersen | 433/6 |
| 5,037,295 | 8/1991 | Bergersen | 433/6 |
| 5,203,695 | 4/1993 | Bergersen | 433/6 |

FOREIGN PATENT DOCUMENTS

| | | | |
|---|---|---|---|
| 2279876 | 1/1995 | United Kingdom | 433/6 |

*Primary Examiner*—Cary E. O'Connor
*Attorney, Agent, or Firm*—Hill & Simpson

[57] ABSTRACT

An orthodontic appliance for assisting in properly positioning teeth within the mouth of an individual which is capable of fitting various mouth and tooth sizes. The appliance includes a labial-buccal flange, a lingual flange spaced from the labial-buccal flange, both of which define a generally U-shaped configuration in the occlusal view, and an isthmus interconnecting the two flanges. At least one tooth trough is defined between the labial-buccal flange and the lingual flange for receiving either an upper or a lower row of the individual's teeth. The appliance includes no individual tooth sockets but instead utilizes pressure applied by the labial-buccal flange, the lingual flange, and the relative angles and material thicknesses to properly position the teeth. The appliance is capable of fitting mouths and teeth of various sizes because it includes no individual tooth sockets. The appliance is also useful as a device for preventing sleep apnea, snoring and bruxism as well as an athletic mouth guard.

31 Claims, 2 Drawing Sheets

APPLIANCE ADAPTED TO FIT MANY MOUTH AND TOOTH SIZES FOR ORTHODONTIC CORRECTION AND OTHER USES

FIELD OF THE INVENTION

The present invention relates to tooth positioning appliances, and in particular to a prefabricated appliance of one size which accommodates various mouth and tooth sizes and is useful as an orthodontic corrective device, an athletic mouthguard, a bruxism inhibitor, and a sleep apnea prevention device and snoring prevention device.

BACKGROUND OF THE INVENTION

There are many tooth malocclusion conditions which are correctable through orthodontic treatment. Some of these conditions include incisal spacing, overjet, overbite, incisal crowding, tooth rotation and improper jaw relations. Metal bands and wires are often used in the permanent dentition stage to provide the desired correction. Thermoplastic removable positioners or appliances are also available such as those disclosed in my prior U.S. Pat. Nos. 4,139,944; 4,919,612; 3,848,335; and 3,939,598.

These removable appliances are typically provided with tooth sockets each for receiving therein one of the individual's teeth for guiding and directing the tooth into a proper occlusal position. Such appliances are therefore selected by measuring the individual's mouth and teeth and matching the appropriate sized appliance having the appropriate tooth socket sizes and spacing.

It would be an improvement in the art if a removable appliance were provided capable of fitting a variety of mouth and tooth sizes and which could therefore be used to initially guide and direct the erupting permanent incisors and other teeth into an individual's mouth to a desirable occlusal condition. In some cases, after an individual's teeth have erupted, it would also be an improvement in the art if an appliance were provided to correct problems with the permanent teeth and to retain these teeth in proper condition.

Custom made devices for preventing sleep apnea, snoring, bruxism and for use as athletic mouthguards require custom modification and are extremely expensive. A device which would perform these functions, accommodate many mouth and tooth sizes and yet still fit an individual properly would be a significant improvement in the art.

SUMMARY OF THE INVENTION

The present invention provides a U-shaped appliance having a tooth receiving trough defined between an outer labial-buccal flange and an inner lingual flange connected by an isthmus or plate. The appliance of the invention incorporates a tooth receiving trough having particular features which eliminate the need for individual tooth receiving sockets and further permits the appliance to accommodate teeth and mouths of different sizes. The present invention also is useful to alleviate snoring by advancing the mandible and opening the mouth slightly while sleeping to prevent the lower jaw and tongue from slipping or being positioned dorsally against the posterior wall of the pharynx allowing the uvula to vibrate when intaking air through the mouth. The present invention by increasing the airway and moving the tongue anteriorly decreases the tendency for sleep apnea, and can also reduce the effects of night grinding or bruxism. The present invention can also serve as an athletic mouthguard during participation in contact sports.

In one embodiment, the labial-buccal flange and inner lingual flange define a maxillary tooth trough between upwardly extending superior segments of the flanges. The maxillary tooth trough has a gradually narrowing width as it approaches the isthmus. This narrower width applies pressure to the incisor teeth as they erupt into an individual's mouth and also when they are fully erupted. By doing so, the appliance assists in guiding the incisors into a correct position and rotational orientation to correct abnormal jaw relations, overjet, overbite, incisal crowding, rotations, open bite and improper spacing conditions. Once the incisors are fully erupted, the appliance can further correct these same problems with the exertion of force by the patient biting down on the appliance. The appliance also serves as protection to the upper and lower anterior teeth from damage during contact sports. It also helps to stabilize the appliance in the mouth if the patient bruxes while sleeping. The appliance maintains the position of the upper and lower tooth troughs securely over the teeth and helps to restrict the lateral jaw movement during tooth grinding and thereby limits the abrasion forces to the flat mating occlusal surfaces of the appliance instead of the enamel occlusal and incisal surfaces of the teeth.

In another embodiment, in the area of the incisors the isthmus is slightly thicker to create an open bite condition between the upper and lower incisors. This slight open bite condition is created by a gradual upward slope in the upper surface of the isthmus and a gradual downward slope in the lower surface of the isthmus in the area of the canines.

In another embodiment, the thickness of the material of the labial-buccal flange in the area of the upper incisors is thinned approaching the upper edge or gingival portion of the upper segment of the labial-buccal flange. The thinned material allows for additional stretching across the area of the incisors creating a tension in the labial-buccal flange which assists in applying pressure to the erupting incisors of an individual for properly positioning the teeth.

In a further embodiment, the labial-buccal flange and inner lingual flange each include superior upwardly extending segments and inferior downwardly extending segments. The superior segments define a maxillary tooth trough for receiving an upper row or group of anterior teeth and the inferior segments define a mandibular tooth trough for receiving the lower row or group of anterior teeth. The inner surfaces of the upper labial-buccal flange and lower-labial buccal flange have a relative angle therebetween which is generally less than the typical angle of an individual's teeth for the mating tooth surfaces. This slightly smaller angle assists in applying further pressure to the individual's teeth as they erupt by properly guiding and directing the teeth to their fully erupted occlusal positions to provide the upper and lower incisors with a more labial inclination so that the angle between the upper and lower incisors is reduced. The smaller angle also aids in preventing overbite relapse by causing the lower incisor edges to make greater firmer contact with the lingual surfaces of the upper incisors.

In a still further embodiment, the upper and lower edges of the superior and inferior labial-buccal segments, respectively, are adapted to avoid contact with the gingival area of the individual's mouth by being tilted outward on the inner surface to clear the gingival tissue regardless of mouth size. This is to prevent gingival recession, especially on the lower tooth arch of an individual which is most susceptible to such a condition.

In a further embodiment, lingual extensions extend from the appliance from the lower lingual flange on either side of the midline to ensure mandibular advancement. This advancement will stimulate more efficient forward mandibular growth in children helping to correct antero-posterior jaw discrepancies present in mandibular retrusion type malocclusions. The lingual extensions are extremely helpful in maintaining a forward position of the mandible while sleeping, which can alleviate sleep apnea and also prevent the tribulation of the uvula which causes snoring by providing a more open airway to the trachea. When the mandible is advanced, it also anteriorly positions the tongue, through the muscular attachment of the tongue to the upper genial tubercle in the anterior segment of the mandible. This moves the tongue away from the posterior pharyngeal wall and increases the volume of air that can pass into the trachea and lungs, reducing sleep apnea and snoring.

With a preformed device that fits any configuration and size of teeth, it can automatically be given to a patient to reduce or eliminate snoring as well as to prevent the effects of bruxism (night grinding) such as excessive abrasion or wear of the teeth and TMJ complications. Since the device is preformed and has a significant labial shield on the upper and lower anterior teeth as well as a great deal of plastic between the arches, it can serve as an efficient mouthguard in contact sports. It protects the teeth from horizontal blows to the lip area as well as from vertical blows from below that knock the mandibular teeth up against the maxillary teeth by forcing the mandible to close suddenly in an unusual manner. It also allows for easy mouth breathing required in most sports. Breathing holes or air passageways can also be placed into the appliance on either side of the split line to increase air intake even when the teeth are closed together into the appliance. This makes snoring more difficult and increases oxygen intake in sleep apnea and during participation in contact sports.

DETAILED DESCRIPTION OF THE PREFERRED EMBODIMENTS

Figure 1:
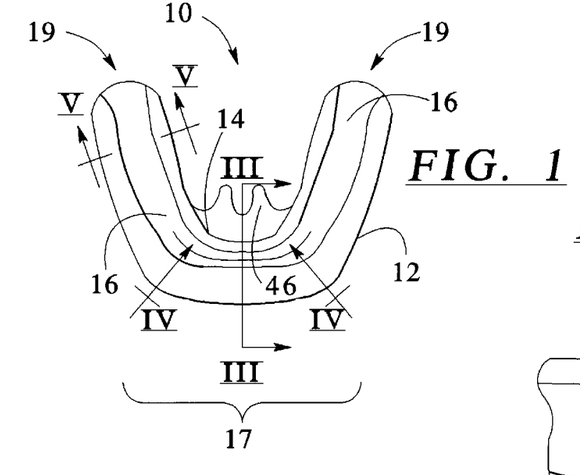
FIG. 1 is an occlusal plan view of an appliance embodying the principles of the present invention.

FIG. 1 illustrates one embodiment of an appliance 10 embodying the principles of the present invention in an occlusal or plan view. The appliance 10 is generally U-shaped to correspond with an upper and a lower arch of a human mouth. The appliance has an outer labial-buccal flange 12 and inner lingual flange 14 both generally vertical and extending superior to and inferior to a connecting isthmus or plate 16. Isthmus 16 interconnects the labial-buccal flange 12 and inner lingual flange 14 and is intended to almost engage the occlusal surfaces of the posterior teeth when the appliance is inserted into a human mouth.

Figures 5, 7:
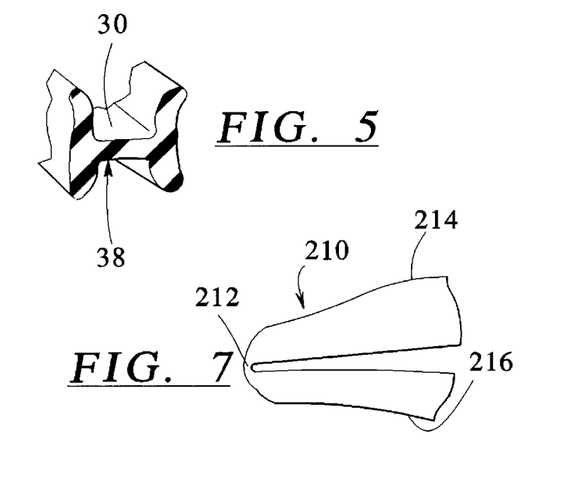
FIG. 5 is a sectional view taken along line V—V of the appliance of FIG. 1.
FIG. 7 is a side elevation of another embodiment of an appliance employing a posterior hinge and embodying the principles of the present invention.
Figure 6:
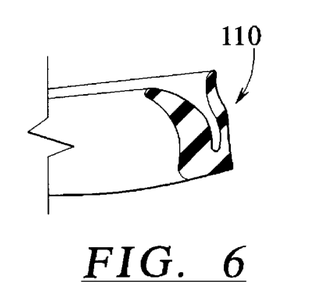
FIG. 6 is a side sectional view of another embodiment of an appliance embodying the principles of the present invention.

The appliance may also be provided for use with only an upper or a lower arch, and in such cases, the flanges would extend only superiorly, or inferiorly, respectively. FIG. 6 illustrates an appliance 110 having only an arch shown in cross-section. An appliance 210 may further be fabricated having a durable living hinge 212 at the posterior distal ends of the appliance connecting otherwise separate superior and inferior segments 214, 216, respectively (FIG. 7). Material selection and thickness may be easily manipulated to control the durability characteristics of the hinge. Preferably, the hinge would exert an opening force between the upper and lower section forcing the wearer to bite down, enhancing the appliances's performance. Each upper and lower section would have its own separate isthmus. The device would have all of the characteristics described herein when in a closed position with the upper and lower segments abutting one another.

Individuals typically go through four stages in their tooth development including a deciduous tooth stage where only deciduous teeth are present. Individuals also go through a mixed dentition stage typically consisting of permanent upper and lower incisors (central and lateral incisors) and first permanent molars, deciduous canines, deciduous first molars and deciduous second molars. The third stage is where all of upper and lower permanent incisors have erupted while the canines and molars exfoliate and are replaced by permanent canines and bicuspids. The fourth stage follows where all of the permanent posterior molar teeth erupt into an otherwise full adult dentition. Appliance 10 is intended for use initially at about age 6 to guide and direct the erupting permanent incisors into the mouth in a proper occlusal fashion. The appliance does so by eliminating or inhibiting tooth rotation and forcing the incisors into their proper positions and at the same time forcing them under their own eruptive forces to significantly and permanently widen and enlarge the arches.

An appliance is also useful as a retainer for any individual until about age 9 at which time the appliance is again useful for guiding and directing the erupting permanent canines and premolars into an ideal Class I occlusion similar to that possible for the incisors at the earlier stages. The same appliance can be used after the upper and lower adult incisors have fully erupted and need straightening. The same appliance is then useful to align these teeth. After this stage of eruption is complete, the appliance 10 is again useful as a retainer from age 8 to about age 10 after which time it can guide the adult canines and premolars into position. At about 11 years and older, the appliance may be used if necessary to maintain proper orientation and position of the teeth. The appliance is also useful for any individuals with fully erupted adult teeth to straighten these teeth as well.

An object of appliance 10 is for each particular size of the appliance to fit many different sizes of teeth and mouths. To accomplish this objective, appliance 10 is provided having generally smooth inner surface in the tooth troughs, thus having no individual tooth sockets but instead having labial-buccal flange 12 and inner lingual flange 14 provided with particular orientations and contours.

Appliance 10 can be made in different lengths measured from an anterior incisal tip 17 to the posterior distal ends 19 as illustrated in FIG. 1 wherein the length is indicated generally as L. The appliance may end at an area corresponding to the upper second deciduous molars if the appliance is to be used in children around the ages of 6 or 7 years prior to eruption of the first permanent molars. The appliance may extend a little further to the area of the upper first permanent molars for use in children from about 7 years of age to about 12 years of age. The ends 19 of the appliance may extend a little further to an area corresponding to the upper second permanent molars for children from the ages of 12 and up.

Figure 2:
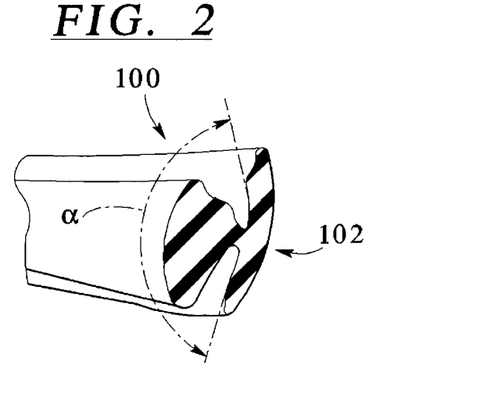
FIG. 2 is a sectional view of a prior art appliance through the anterior portion of the appliance.
Figure 3:
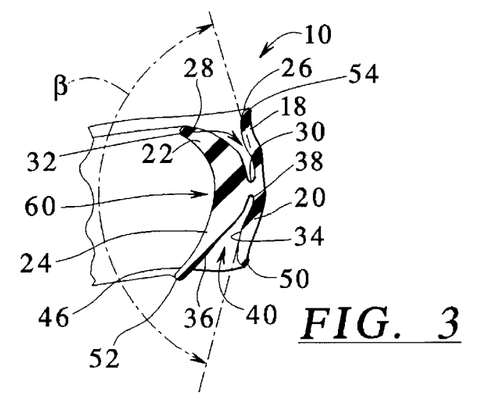
FIG. 3 is a sectional view taken generally along line III—III of FIG. 1 through the anterior portion of the appliance.

Returning to the drawings, FIG. 2 illustrates a typical prior art cross-section through the anterior incisal portion 102 of an appliance 100 whereas FIG. 3 illustrates a cross-section through the anterior portion 17 of appliance 10 of the invention. Outer labial-buccal flange 12 includes an upwardly extending superior segment 18 and a downwardly extending inferior segment 20 relative to isthmus 16. Similarly, inner lingual flange 14 includes a superior segment 22 and an inferior segment 24.

Superior segments 18 and 22 include an inner labial surface 26 and inner lingual surface 28, respectively, which face or confront one another. Isthmus 16 includes an upper surface 30 and cooperates with inner surfaces 26 and 28 of the superior segments to define a maxillary tooth trough 32 having a varying width around the U-shaped appliance 10. Similarly, inferior segments 20 and 24 define an inner labial surface 34 and inner lingual surface 36, respectively, which confront or face one another. Isthmus 16 also has a lower surface 38 which corresponds with inner surfaces 34 and 36 to define a mandibular tooth trough 40 also having a varying width around the U-shaped appliance. The width is defined for both the maxillary and mandibular tooth troughs 32 and 40 as the distance between their respective inner surfaces.

As illustrated in FIGS. 2 and 3, the appliance of the invention includes an increased inclination relative to vertical of the inner labial surfaces 26 and 34. Typically in the average child, the angle between the labial surfaces of the upper and lower central incisors is about 131°. A typical prefabricated appliance for applying pressure against the incisors includes an angle between the upper and lower central incisors which is greater than 131° or usually between 135° and 138° as shown in FIG. 2. This is done to place pressure upon the incisors as close to a vertical direction as possible. This high angulation in a typical appliance however defeats the correction and retention of an overbite condition since the lingual surfaces of the upper incisors are more vertically oriented in comparison to the lower incisors and provide less resistance to relapse. When a child is at an early age, this angulation can be altered in erupting incisors very easily. Angulation of the incisors can therefore be altered to encourage the upper central and lateral incisors to erupt with an increased labial slant. Appliance 10 of the invention therefore provides decreased angulation between inner labial surface 26 and inner labial surface 34, for example in a range of 115° to 131°.

Figure 4:
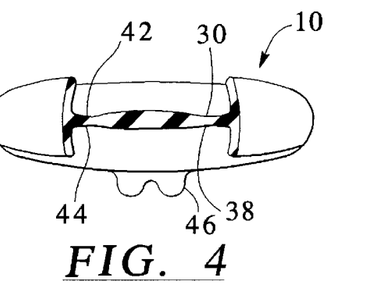
FIG. 4 is a fragmentary front sectional view taken along arc IV—IV of the appliance of FIG. 1.

FIG. 4 illustrates a front sectional view along the arc of the tooth troughs of appliance 10 to illustrate another advantage of the invention. The primary thickness of isthmus 16 is generally of a constant dimension except in the incisor area 17 of both the upper and lower arch. As is illustrated in FIG. 4, the upper isthmus surface 30 includes a slight upward step in the area of the lateral and canine upper teeth. Similarly, lower isthmus surface 38 includes a slight downward step 44 in the area of the lateral and canine lower teeth. Upward step 42 of isthmus 16 is preferably more accentuated than the downward step 44 to cause the upper incisors of an individual to fit up into the smile more efficiently to more effectively eliminate a gummy smile. The increased thickness over the primary thickness of isthmus 16 in the incisor area 17 defined between the steps 42 and 44 also helps to reduce overbite in individuals more completely and further helps to prevent its relapse. The steps 42 and 44 are essentially set up in one embodiment so that the appliance 10 creates a slight tendency towards an open-bite condition on the order of about 0.5 mm in the incisor area 17.

As is illustrated in FIG. 1, appliance 10 may also include one or more large inwardly extending lingual tongue or extensions 46 protruding from inner lingual flange 14 away from inferior segment 24. Lingual extension 46 is preferably disposed at about the midline on appliance 10 defined as an extension from inferior segment 24, and also preferably extends downward about 5 to 15 mm. If appliance 10 is adapted having only a mandibular tooth trough, the lingual extension preferably extends from the inner-lingual flange in a similar position to the combination or all in one appliance having upper and lower segments. The lingual extension may include a single portion or 2 segments disposed side-by-side with a middle slot permitting room for the mid-line frenum of the tongue therebetween and permitting longer lingual extension segments.

Lingual extensions 46 assist in keeping the mandible of the individual advancing maximally at all times and moving forward. For producing a forward mandible force, the most important tooth margins are the lower lingual contact surface and upper labial contact surface at the anterior portion of appliance 10. It is therefore important that inferior or lower inner lingual surface 36 and superior or upper inner labial surface 26 are supported by sufficient appliance material to maintain their relative positions when appliance 10 is inserted in an individual's mouth.

The lower inner labial surface 34 and upper inner lingual surface 28 are relatively unimportant margins for producing mandible advancement and therefore the height of the inferior edge 50 of labial inferior segment 20 may be reduced significantly. This reduction in height also reduces the risk of gingival contact with inferior segment 20 in the lower labial gingival area. It is important when producing an appliance which is intended to fit various sized teeth and mouths that the likelihood of gingival contact be reduced or prevented. This is to prevent gingival recession of the lower incisors. It is therefore preferable that the height of lower or inferior labial-buccal segment 20 of appliance 10 is on the order of about 6 mm extending from isthmus lower surface 16 to inferior edge 50.

It is also preferred that inferior lingual segment 24 is slanted or tapered away from the gingival margin toward its distal or inferior edge 52. A taper essentially prevents any gingival contact regardless of the size of the soft tissues of an individuals mouth. A similar taper may be added to the superior segment 22 of inner lingual flange 14 to surface 28 to prevent similar gingival recession in the upper anterior arch. Also, the posterior distal ends 19 of the labial-buccal flange 12 and inner lingual flange 14 are preferably tapered or slanted away from the gingival margins at their respective upper edges from about the location beyond incisor area 17 through the distal ends 19 of the appliance to avoid contact with gingival tissue.

An additional advantage of the present invention is also illustrated in FIG. 3. It is preferred that the appliance 10 be resilient and able to stretch considerably in the incisal area 17 between the canines of the upper arch from about 3 to about 7 mm. A typical prefabricated appliance is able to stretch only about a maximum of 3 mm. To accomplish the desired additional stretching, the material thickness of the upper labial flange 12 is produced having a relatively thin cross-section. The material thickness of superior segment 18 adjacent the isthmus 16 must be substantial enough to provide support and position retention for the incisors as they erupt downward. A distal or superior edge 54 of superior segment 18 however is reduced relative to that of the prior art appliance to a thickness of about 1 mm to 3 mm. The material is thinned from the outer surface of the flange so as not to alter the contour of inner labial surface 26 which is intended to closely approximate the labial surface of the teeth. The thin wall cross-section of the upper portion of labial-buccal flange 12 combined with the increased inclination as described above provides for the upper portion of labial-buccal flange 12 to stretch. This tension exerts a force across the incisor area to aid in rotating the incisors more forcefully and to space the incisors closer together. The incisal area 17 of inferior segment 20 may be similarly thinned as well.

Stretching of the appliance across the incisal area also increases the ability of the appliance to stay in the mouth without slipping off of the teeth. This is particularly helpful in nighttime retention and use as a preventative sleep apnea and anti-snoring device. It also increases the retainability when it is used as a mouthguard in active or contact sports.

The appliance may also be provided with a distance across either or both arches which is narrower than an average person's mouth. This would also assist in applying pressure to the teeth.

As best illustrated by a comparison of FIGS. 2 and 3, the incisal or anterior portion 17 of the maxillary tooth trough 32 of appliance 10 is narrower than in the prior art appliance to apply force to the incisors at an early stage of eruption, for example, when about ⅓ to ½ erupted. This narrower tooth trough allows for force to be exerted on the crown of the incisors for a longer period of time during eruption. This also places greater lateral force on the teeth across the incisor arch to maintain a greater amount of natural expansion as the teeth erupt. This is accentuated by the stretch of the upper labial-buccal flange in the anterior or incisor area as described above. The narrowed trough 32 also somewhat inhibits or slows the vertical descent of the incisors to assist in correcting overbite conditions. The tooth trough widens beyond the incisal area 17 permitting the appliance to fit various sizes of teeth and mouths. This narrowing of troughs 32 and 40 also increases the retainability of the appliance to the teeth preventing it from slipping away from these teeth.

Maxillary tooth trough 32 preferably has a width in the incisor area 17 between inner labial surface 26 and inner lingual surface 28 of about 1 mm measured upward from upper surface 30 of isthmus 16 for a distance of about 2 mm. Trough 32 preferably then widens to about 2 mm for the next 3 mm upward from upper surface 30 of t he isthmus. By comparison, a typical prefabricated appliance as illustrated in FIG. 2 generally has a tooth trough width in the incisor area of about 2 mm adjacent the upper surface of the isthmus which widens to about 4 mm as it approaches the upper edges moving upward. The width of the tooth trough 32 and 40 in the area of the incisors 17 can also be widened greater than the amounts given above to accommodate crowded teeth in individuals using the appliance to reduce sleep apnea and snoring as well as for a sports mouthguard.

The upper surface 30 of the isthmus 16, from the midline, remains knife edge thin or narrow and begins to widen at a distance 17 mm from the midline measured along the labial and buccal edge at each side to accommodate an upper permanent central and lateral incisor from 12.4 mm up to 19 mm in mesio-distal width. This upper isthmus surface 30 begins widening on the lingual so that at 22 mm from the midline it is 3 mm wide bucco-lingually, and will accommodate a first upper premolar of the smallest size of teeth, and an upper canine of the largest size of teeth. At 28 mm from the midline, the width bucco-lingually is 6 mm and will accommodate an upper second premolar of the smallest size of teeth and a first premolar of the largest. At 45 mm from the midline on the upper segment, the upper isthmus surface 30 is 9 mm wide and will accommodate an upper second permanent molar of the smallest sized teeth and an upper first permanent molar of the largest.

In the lower trough 40 a similar situation exists where at 11 mm from the midline along the curve of the arch, the lower surface 38 of the isthmus 16 begins to widen on the lingual portion of the arch. This knife-edge thin or narrow lower isthmus surface 38 corresponding to the incisal edges of the lower incisors will accommodate a lower permanent central and lateral incisor whose combined mesio-distal widths are from 9.4 mm to 13.7 mm in width. This lower isthmus surface 38 begins widening on the lingual so that at 17 mm from the midline it is 3 mm wide labio-lingually and will accommodate a lower first premolar of the smallest size of teeth and a canine of the largest size. At 23 mm from the midline, the width bucco-lingually is 6 mm and will accommodate a lower second premolar of the smallest size of mouth and teeth and a lower first premolar of the largest. At 41 mm from the midline, the bucco-lingual width is 9 mm and will accommodate a lower second molar of the smallest size of mouth and teeth and a first molar of the largest.

In an additional embodiment, appliance 10 includes a comfortable concavity 60 disposed on the lingual portion of the appliance as shown in FIG. 3. The concavity extends in one embodiment across the incisal area 17 from canine to canine. The concavity 60 is a depression adapted for receiving an individual's tongue therein to help remind the individual where the tongue should rest when the appliance is worn. This also enables the tongue to be positioned forward as the mandible is held forward by the appliance to aid in correction of sleep apnea and snoring.

Figure 8:
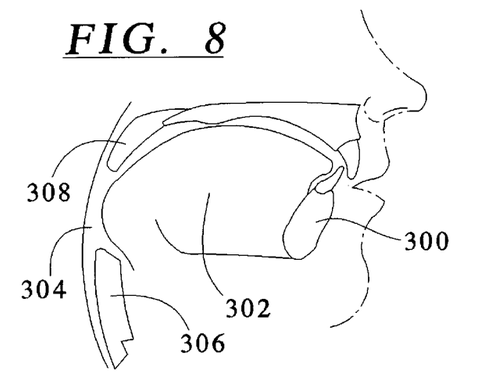
FIG. 8 is a fragmentary sectional side elevation of an individual with disruptive snoring and obstructive sleep apnea conditions showing the almost closed airway passage in the pharynx.
Figure 9:
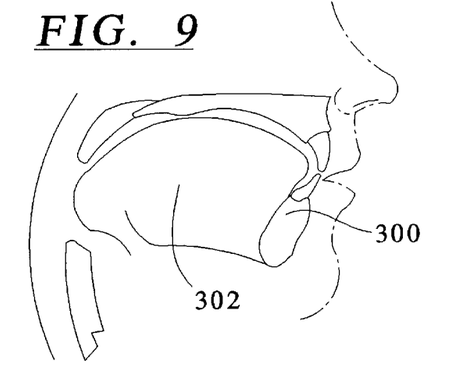
FIG. 9 is a fragmentary sectional side elevation of the same individual wearing an appliance of the present invention showing an open airway and unrestricted pharyngeal opening.

How the appliance helps to prevent sleep apnea and snoring is best illustrated in FIGS. 8 and 9. FIG. 8 illustrates an individual's jaw position when sleep apnea is a problem. The mandible or jaw 300 is positioned rearward which pushes the tongue 302 rearward as well. The tongue 302 partially blocks the pharynx 304 by being closely spaced to the trachea 306. With this narrow space, less air passes causing the uvula 308 to vibrate or quiver which results in snoring.

Figure 10:
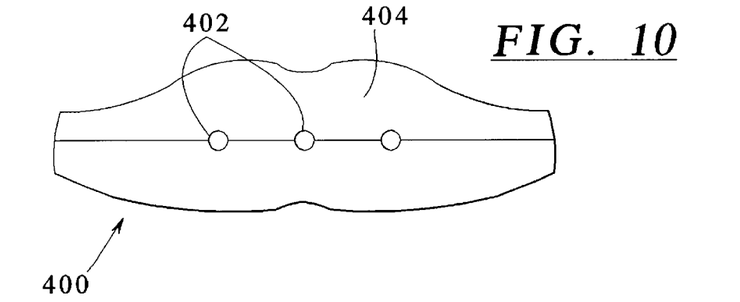
FIG. 10 is a front view of an appliance of the present invention including a plurality of air passageways formed transversely through the isthmus.
Figure 11:
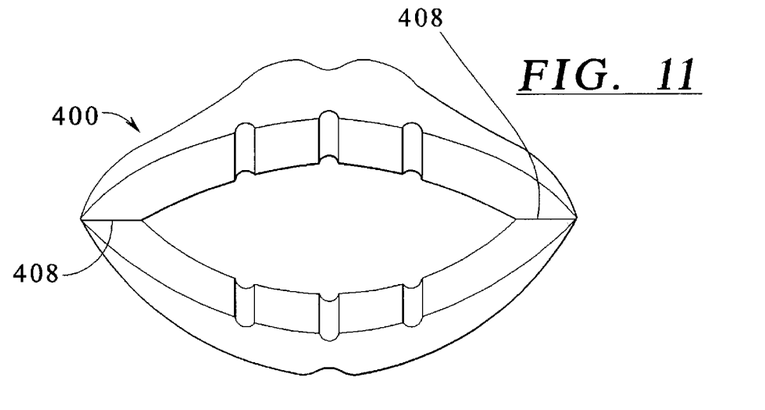
FIG. 11 is a front elevational view of the appliance of FIG. 10 shown in an open condition.
Figure 12:
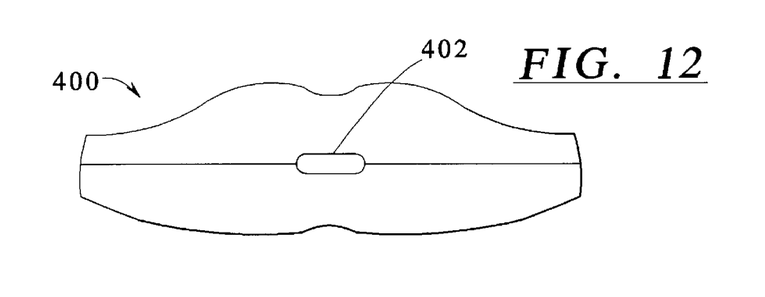
FIG. 12 illustrates an appliance of the present invention illustrating a single air passageway formed through the isthmus.

By wearing the appliance 10, the mandible 300 and tongue 302 are more properly positioned forward as illustrated in FIG. 9. This increases the space between the tongue 302 and trachea 306, opening the pharynx 304. This in turn allows more air to pass, preventing the uvula 308 from quivering. By providing large breathing holes or air passageways at the split line between the upper and lower halves or segments, with half of each hole in the upper segment and half in the lower, this increases air intake while wearing the device. FIG. 10 illustrates an appliance 400 having a plurality of air passageways 402 extending through the isthmus of the appliance between the outer labial buccal flange 404 and inner lingual flange (not shown). As will be evident to those skilled in the art, these air passage ways 402 may be added through the isthmus of a device constructed as illustrated in FIG. 3. The device includes upper and lower tooth troughs which do not separate into two separate segments. Alternatively, as is illustrated in FIG. 11 the air passageways 402 may be formed in an appliance which opens via a posterior hinge 408 similar to the device shown in FIG. 7. FIG. 12 merely illustrates that only a single air passageway 402 may be incorporated into an appliance 400 as well. The single passageway or a central passageway of several also assists in permitting the user's tongue to move further forward enhancing proper jaw placement and the sleep apnea and snoring prevention aspects of the invention.

Appliance 10 of the present invention by incorporating the features described above may be utilized for prevention or early correction of incisal spacing problems, overjet, overbite, tooth overcrowding, and improper tooth rotation. The tight spacing of the tooth trough width in the area of the incisors along with the increased incline of the upper labial flange, in combination with the stretching across the upper incisor area assists in correcting these problems as the permanent teeth erupt in an individual. The fact that appliance 10 includes no individual tooth sockets allows each size of appliance to fit many tooth and mouth sizes. The appliance is also useful as an athletic mouthguard, for prevention of bruxism or nighttime teeth grinding, and for prevention of sleep apnea or snoring as described.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An orthodontic appliance comprising:
    a labial-buccal flange having a generally U-shaped configuration and a generally smooth inner labial surface;
    a lingual flange also having a generally U-shaped configuration and generally smooth inner lingual surfaces being spaced from said inner labial surface of said labial-buccal flange;
    an isthmus interconnecting said labial-buccal flange and said lingual flange;
    a tooth receiving trough defined adjacent said isthmus between-said inner labial surfaces and said inner lingual surface for receiving at least one of an upper or a lower row of teeth, said tooth receiving trough sized to act as a sole means for retaining the orthodontic appliance in an individual's mouth; and
    wherein said tooth receiving trough in an incisor area has a width which narrows toward said isthmus sufficient to apply pressure against an individual's incisors as said incisors erupt.

2. The orthodontic appliance of claim 1 wherein said tooth receiving trough comprises a maxillary tooth trough for receiving an upper row of teeth.

3. The orthodontic appliance of claim 1 wherein said tooth trough comprises a mandibular tooth trough for receiving a lower row of teeth therein.

4. The orthodontic appliance of claim 1 wherein said labial-buccal flange and said lingual flange each comprise a superior segment extending upward from said isthmus and an inferior segment extending downward from said isthmus, said superior segment defining therebetween a maxillary tooth trough for receiving therein an upper row of teeth, and said inferior segments defining therebetween a mandibular tooth trough for receiving therein a lower row of teeth, wherein at least one of said maxillary tooth receiving trough and said mandibular tooth receiving trough in an incisor area has a width which gradually narrows approaching said isthmus to apply pressure to corresponding incisors of said individual as said incisors erupt.

5. The orthodontic appliance of claim 4 wherein said isthmus further comprises an upper isthmus interconnecting said superior segments of said labial-buccal flange and said lingual flange and a lower isthmus interconnecting said inferior segments of said labial-buccal flange and said lingual flange, and a hinge joining said upper isthmus and said lower isthmus at the posterior distal ends thereof.

6. The orthodontic appliance of claim 4 wherein the other of said maxillary or mandibular tooth receiving troughs in said incisor area has a width which gradually narrows toward said isthmus to apply pressure to said individual's corresponding incisors as said incisors erupt.

7. The orthodontic appliance of claim 6 wherein said width of said other of said maxillary or mandibular tooth receiving troughs is adapted to restrict tooth eruption in said incisor area as teeth corresponding thereto in said individual's mouth are about ⅓ to ½ erupted.

8. The orthodontic appliance of claim 6 wherein said width is about 1 mm or less adjacent said isthmus for a distance of about 2 mm or greater therefrom.

9. The orthodontic appliance of claim 4 wherein said width of either said maxillary or mandibular tooth receiving trough is adapted to restrict tooth eruption in said incisor area as teeth corresponding thereto in said individual's mouth are about ⅓ to ½ erupted.

10. The orthodontic appliance of claim 4 wherein said upper and lower surfaces of said isthmus define a primary thickness therebetween and define an increased thickness therebetween in said incisor area of said appliance.

11. The orthodontic appliance of claim 10 wherein said increased thickness is about 1 mm or more greater than said primary thickness of said isthmus.

12. The orthodontic appliance of claim 4 wherein said inferior labial and lingual segments are adapted to prevent contact with a gingival area of said individual's mouth.

13. The orthodontic appliance of claim 12 wherein said inferior lingual segment extends downward from said lower surface of said isthmus to a lower edge a height sufficient to avoid contact with said gingival area of said individual.

14. The orthodontic appliance of claim 12 wherein said inferior labial segment is tapered outward from said mandibular tooth trough adjacent a lower edge to avoid contact with said gingival area of said individual.

15. The orthodontic appliance of claim 4 wherein said superior labial and lingual segments are adapted to prevent contact with a gingival area within said individual's mouth.

16. The orthodontic appliance of claim 15 wherein said superior lingual segment extends downward from said maxillary tooth trough toward an upper end height sufficient to avoid contact with said gingival area of said individual.

17. The orthodontic appliance of claim 15 wherein said superior labial segment is tapered outward from said maxillary tooth trough adjacent an upper end to avoid contact with said gingival area of said individual.

18. The orthodontic appliance of claim 4 further comprising one or more lingual extensions projecting from said lingual flange.

19. The orthodontic appliance of claim 4 further comprising a lingual concavity formed in said lingual flange.

20. The orthodontic appliance of claim 4 wherein said inner lingual surface of one of said maxillary tooth receiving trough and said mandibular tooth receiving trough tapers away from said inner labial surface such that said orthodontic appliance laterally accommodates in said incisor area at least part of a canine tooth of a mouth of a larger person or a whole canine tooth of a mouth of a smaller person.

21. The orthodontic appliance of claim 20 wherein said inner lingual surface tapers away from said inner labial surface on the other of said maxillary or mandibular tooth receiving troughs such that said orthodontic appliance accommodates at least part of a canine tooth of a mouth of a larger person or a whole canine tooth of a smaller person.

22. The orthodontic appliance of claim 4 further comprising one or more air passageways formed transversely through said isthmus extending between said lingual flange and said labial-buccal flange.

23. The orthodontic appliance of claim 1 wherein the appliance is one of a corrective orthodontic device, an anti-snoring device, a device to prevent bruxism, a device to prevent sleep apnea, and an athletic mouth guard.

24. An orthodontic appliance for use in a mouth of an individual comprising:
   a labial-buccal flange having a generally U-shaped configuration and an inner labial surface;
   a lingual flange also having a generally U-shaped configuration and an inner lingual surface being spaced from said inner labial surface of said labial-buccal flange;
   an isthmus interconnecting said labial-buccal flange and said lingual flange;
   at least one tooth receiving trough defined adjacent said isthmus between said inner labial surfaces and said inner lingual surface for receiving at least one of an upper or a lower row of teeth; and
   wherein said tooth receiving trough in an incisor area has a width which narrows toward said isthmus sufficient to apply pressure against an individual's incisors as said incisors erupt and said width is about 1 mm or less adjacent said isthmus for a distance of about 2 mm or greater therefrom.

25. An orthodontic appliance for use in a mouth of an individual comprising:
   a labial-buccal flange having a generally U-shaped configuration and an inner labial surface;
   a lingual flange also having a generally U-shaped configuration and an inner lingual surface being spaced from said inner labial surface of said labial-buccal flange;
   an isthmus interconnecting said labial-buccal flange and said lingual flange;
   at least one tooth receiving trough defined adjacent said isthmus between said inner labial surfaces and said inner lingual surface for receiving at least one of an upper or a lower row of teeth; and
   wherein said tooth receiving trough in an incisor area has a width which narrows toward said isthmus sufficient to apply pressure against an individual's incisors as said incisors erupt and said width is greater than 1 mm adjacent said isthmus for a distance of about 2 mm or greater therefrom.

26. An orthodontic appliance for use in a mouth of an individual comprising:
   a labial-buccal flange having a generally U-shaped configuration, a superior labial segment having an inner labial surface, and an inferior labial segment having an inner labial surface;
   a lingual flange having a generally U-shaped configuration, a superior lingual segment having an inner lingual surface being spaced from said inner labial surface of said superior labial segment, an inferior lingual segment having an inner lingual surface spaced from said inner labial surface of said inferior labial segment;
   an isthmus interconnecting said labial-buccal flange and said lingual flange and having an upper isthmus surface and a lower isthmus surface;
   a maxillary tooth receiving trough defined by said upper isthmus surface between said inner labial surface and said inner lingual surface of said superior segments;
   a mandibular tooth receiving trough defined by said lower isthmus surface between said inner labial surface and said inner lingual surface of said inferior segments;
   wherein one of said maxillary tooth receiving trough and said mandibular tooth receiving trough in an incisor area has a width which narrows toward said isthmus sufficient to apply pressure against an individual's incisors as said incisors erupt; and
   wherein said inner labial surface of said superior labial segment and said inner labial surface of said inferior labial segment are inclined relative to one another defining an angle therebetween which is less than that of average incisors adapted to receive therein varying shapes and sizes of teeth, and further adapted to assist in guiding said teeth to their proper occlusal position.

27. The orthodontic appliance of claim 26 wherein said inner labial surfaces are inclined relative to one another at an angle less than 131°.

28. The orthodontic appliance of claim 26 wherein said inner labial surfaces are inclined relative to one another at an angle between about 115° to about 131°.

29. An orthodontic appliance for use in a mouth of an individual comprising:
   a labial-buccal flange having a generally U-shaped configuration, a superior labial segment having an inner labial surface, and an inferior labial segment having an inner labial surface;
   a lingual flange having a generally U-shaped configuration, a superior lingual segment having an inner lingual surface being spaced from said inner labial surface of said superior labial segment, an inferior lingual segment having an inner lingual surface spaced from said inner labial surface of said inferior labial segment;
   an isthmus interconnecting said labial-buccal flange and said lingual flange and having an upper isthmus surface and a lower isthmus surface;
   a maxillary tooth receiving trough defined by said upper isthmus surface between said inner labial surface and said inner lingual surface of said superior segments;
   a mandibular tooth receiving trough defined by said lower isthmus surface between said inner labial surface and said inner lingual surface of said inferior segments;

wherein one of said maxillary tooth receiving trough and said mandibular tooth receiving trough in an incisor area has a width which narrows toward said isthmus sufficient to apply pressure against an individual's incisors as said incisors erupt; and wherein said superior labial segment in said incisor area has a thin wall thickness adapted to permit said labial-buccal flange in said incisor area to stretch thereacross to a degree sufficient to apply pressure to upper incisors of said individual's mouth.

30. The orthodontic appliance of claim 29 wherein a portion of said labial-buccal flange in said incisor area has a wall thickness of about 1 mm to 3 mm.

31. The orthodontic appliance of claim 29 wherein said labial-buccal flange in said incisor area is adapted to stretch from about 3 mm to about 7 mm beyond its natural unstretched state.

* * * * *

UNITED STATES PATENT AND TRADEMARK OFFICE
CERTIFICATE OF CORRECTION

PATENT NO.    : 5,876,199
DATED         : March 2, 1999
INVENTOR(S)   : Dr. Earl O. Bergersen It is certified that error appears in the above-identified patent and that said Letters Patent is hereby corrected as shown below:

In the patent, claim 4, line 5 reads "segment"; should read --segments--.

Signed and Sealed this

Sixteenth Day of January, 2001

Attest:

Q. TODD DICKINSON

Attesting Officer          Commissioner of Patents and Trademarks